United States Patent [19]

Grodberg

[11] Patent Number: 5,156,845
[45] Date of Patent: Oct. 20, 1992

[54] DRY MOUTH LOZENGE

[75] Inventor: Marcus G. Grodberg, Newton, Mass.

[73] Assignee: Colgate-Palmolive Company, Piscataway, N.J.

[21] Appl. No.: 519,073

[22] Filed: May 4, 1990

[51] Int. Cl.⁵ .............................................. A61K 9/68
[52] U.S. Cl. ................................... 424/440; 424/464; 424/493
[58] Field of Search ....................... 424/440, 493, 464; 562/575; 426/548, 650

[56] References Cited

U.S. PATENT DOCUMENTS

| | | | |
|---|---|---|---|
| 4,169,885 | 10/1979 | Raaf | 424/440 |
| 4,196,189 | 4/1980 | Raaf | 424/440 |
| 4,447,412 | 5/1984 | Bulton | 424/498 |
| 4,650,664 | 3/1987 | Schepky | 424/494 |
| 4,652,711 | 3/1987 | Hirsbrunner et al. | 562/575 |
| 4,820,506 | 4/1989 | Kleinberg et al. | 424/493 |
| 4,828,820 | 5/1989 | Glass | 424/440 |
| 4,997,654 | 3/1991 | Corsell et al. | 424/440 |

Primary Examiner—Thurman K. Page
Assistant Examiner—D. Colucci
Attorney, Agent, or Firm—Paul Shapiro; Robert C. Sullivan

[57] ABSTRACT

A dry mouth lozenge comprising a base, a pharmaceutically acceptable acedulate, such as a natural sweetener, betaine hydrochloride and a phramaceutically acceptable fluoride.

11 Claims, No Drawings

DRY MOUTH LOZENGE

BACKGROUND OF THE INVENTION

1. Field of the Invention

This invention relates to a dry mouth lozenge and, more particularly, to a medication for stimulating the flow of saliva.

2. Description of the Prior Art

The flow of saliva in the human mouth can become attenuated to the point that discomfort, incomplete digestion of foods and swallowing problems occur. Various compositions have been tried to alleviate the condition. This dry mouth condition is brought about by numerous reasons, including advancing age, drug, alcohol and nicotine abuse, excessive deposits associated with the salivary glands and their ducts of minerals, such as calcium and as side effects in the use of many commonly used prescription medications, such as antidepressants, anti-hypertensives and anti-histamines, among others.

The U.S. Pat. No. 4,088,788 to Ream, issued May 9, 1978 for "Saliva Stimulating Chewing Gum Composition," discusses the use of a chewing gum composition and an organic duct to stimulate salivation. In another United States Patent to Ream, U.S. Pat. No. 4,151,270, issued Apr. 24, 1979, for "Chewing Gum Composition," the same problem is solved which was directed to the "cotton mouth" effect felt by athletes while exercising.

U.S. Pat. No. 4,400,372 to Muhler, issued Aug. 23, 1983, for "Chewing Gum," and U.S. Pat. No. 4,568,537 to Hoerman, issued Feb. 4, 1986 for "Dental Health Method Employing Chewing Gum," discloses the use of an acid containing substance in chewing gum for promoting salivation. These patents are primarily directed to dental hygiene.

Chewable products for promoting salivation are disclosed in U.S. Pat. No. 2,812,256, issued Nov. 5, 1957, for "Saliva Control Composition." These products produce an alkaline saliva. These compositions utilize beeswax or paraffin.

U.S. Pat. No. 3,312,594 to Cyn, issued Apr. 4, 1967, for "Long Lasting Troche," and U.S. Pat. No. 4,624,849 to Toogood, issued Nov. 25, 1986, for "Antimicrobial Lozenges," disclose lozenges for administering various medicaments.

The use of fluoride ion in chewing gum bases is disclosed in U.S. Pat. No. 4,265,877 to Tental, issued May 5, 1981, for "Composition Containing Sodium Fluoride in a Chewing Gum Base."

No patent discloses the combination of two essential components, which can stimulate the flow of saliva for at least a period of two hours and can treat a chronic condition of dry mouth apart from that brought on by exercising. The composition includes an acedulant, such as betaine hydrochloride, to stimulate the flow of saliva and the use of a fluoride in combination with the betaine hydrochloride to prevent the demineralization of tooth enamel.

Accordingly, it is the object of the present invention to provide a long lasting and effective treatment for chronic cases of dry mouth.

A further object of the invention is to provide a composition which will prevent demineralization of the tooth enamel in the patient's mouth while permitting a long lasting and effective alleviation of dry mouth.

SUMMARY OF THE INVENTION

The present invention relates to a dry mouth lozenge to overcome temporary or substantially permanent dry mouth condition brought about by drug, alcohol or nicotine abuse, disease or injury, or resulting from use of certain medications, which includes a base, a sugarless sweetener, an acedulant, such as betaine hydrochloride, and a fluoride, such as sodium fluoride or sodium monofluorophosphate, for inhibiting erosion of tooth enamel.

DETAILED DESCRIPTION OF THE INVENTION

The present invention envisions a medication to overcome "Dry Mouth" caused by drug, alcohol or nicotine abuse, aging, mineral deposits and side effects of various medications.

According to United States government literature (Fact Sheet—"Dry Mouth (Xerostomia)," National Institute of Dental Research, 1986), "Over 300 commonly used drugs list dry mouth as a side effect. The main culprits are antihypertensives (for high blood pressure) and antidepressants. Both are prescribed for millions of Americans. However, painkillers, tranquilizers, diuretics, and even over-the-counter antihistamines, also decrease saliva."

In addition, radiation treatment for tumors in the head and neck region can permanently damage salivary glands and cancer chemotherapy can cause changes in the composition of the saliva which create the sensation of dry mouth.

Salivary gland diseases, such as Sicca syndrome (Sjogren's disease), also result in dry mouth. Other illnesses responsible for oral dryness are dry gland disease, polyglandular failure dysfunction, neuropathies, other autoimmune disorders, and hyperlipoproteinemia type V. Moreover, such conditions as bone marrow transplants, endocrine disorders, and nutritional deficiencies, such as anemia, can cause dry mouth.

Finally, other causative changes which are responsible for dry mouth include nerve damage due to trauma to the head and neck area resulting from surgery or wounds, and changes in the ability to perceive oral sensations may be brought on by stroke or conditions like Alzheimer's disease.

As a result, The National Institute for Dental Research opened a Dry Mouth Clinic in 1983 for the evaluation, diagnosis and treatment of dry mouth patients. The following have been recommended to relieve dry mouth symptoms:

1. Water or sugar-free carbonated drinks or artificial salivas.
2. Sugarless chewing gum, lozenge mints or hard candies.
3. Lemon rinds or cherry pits for mouth sucking.

Obviously, all of these materials have only a limited effect and often act for only a short time. Furthermore, certain "sourball" candies may stimulate salivary flow, but may also result in the demineralization of tooth enamel. Also, an experimental drug (pilocarpine) appears to be effective, but is not without side effects.

It is, therefore, apparent that a superior product is needed to overcome the limitations of existing treatments. The present invention contemplates such a composition in the form of a lozenge or a buccal tablet which can be sucked in the mouth for up to two hours or more at a time without harmful effects.

The new composition contains noncariogenic natural sweeteners (such as, sorbitol and mannitol), a pharmaceutical acidulant (such as tartaric acid, citric acid, fumaric acid and betaine hydrochloride) to stimulate salivary flow, and a low dose of fluoride (providing, for example, 0.25 mg F per dose) to prevent demineralization of tooth enamel. The amount of fluoride should provide about 0.2 to 2 mg $F^-$. per day. Obviously the amount in any batch or unit dosage will vary depending on unit dosage weight. A convenient amount of fluoride ($F^-$) may be 0.1 mg per unit dosage taken two to ten times a day up to about 0.3 mg or more, e.g. 0.5, 0.6, 0.7, 0.8, 0.9 and 1.0 mg taken less frequently. Furthermore, the incorporation of a special base, such as sugarless chewing gum granulation, not only provides a chewing gum residue, but unexpectedly retards the dissolution of the lozenge in the mouth for up to two hours or more. Other base materials, such as carnauba wax, beeswax or the like may be used. This allows for prolonged stimulation of salivary flow, which can be repeated several times a day, such as after meals and at bedtime, when dry mouth symptoms are at their worst.

EXAMPLE I

| Content of One Tablet | Ingredients | Batch Formula Weight |
| --- | --- | --- |
| 277.6975 mg | Sorbitol Powder USP | 277.697 gm |
| 89.15 | Mannitol Powder USP | 89.1 gm |
| 0.5525 mg | Sodium Fluoride USP | 552.5 mg |
| 17.1 mg | Betaine HCL | 17.1 gm |
| 70.0 mg | Sodium Biphosphate USP | 70.0 gm |
| 20.0 mg | Flavor Orange WJ2808 | 20.0 gm |
| 0.5 mg | FD&C Yellow #6Alum Lake 27% | 0.5 gm |
| 15.0 mg | Povidone USP | 15.0 gm |
| 500 mg | Gum Base | 500 gm |
| 20 mg | Magnesium Stearate USP | 20 gm |
| 1010 mg | | 1010 gm |

It is to be noted that the gum base material may comprise the following formulation:

EXAMPLE II

| | |
| --- | --- |
| 33.0% | Novagum Base |
| 59.8% | Sorbitol |
| 6.7% | Mannitol |
| 0.5% | Flavor (Menthol Cherry) |
| 5% | Corn Starch (added at the end) |

In the foregoing examples, sodium monofluorophosphate (MFP) is used in about equivalent amounts or about 1.7 mg MFP in lieu of 0.55 mg NaF.

The weight ratio of fluoride to acedulant may vary from about 1:5 to 1:200 and preferably 1:10 to 1:100 and most preferably 1:20 to 1:75.

What is claimed is:

1. A dry mouth lozenge comprising a pharmaceutically acceptable gum base, a non-cariogenic sweetener, betaine hydrochloride and a fluoride.

2. A lozenge as disclosed in claim 1, wherein said sweetener is mannitol.

3. A lozenge in accordance with claim 1, wherein said sweetener is sorbitol.

4. A dry mouth lozenge in accordance with claim 1, wherein said sweetener comprises sorbitol and mannitol.

5. A lozenge according to claim 1, wherein the ratio of the weight of betaine hydrochloride to fluoride is from 1:5 to 1:50.

6. A lozenge according to claim 1, wherein the fluoride is sodium fluoride or MFP.

7. A lozenge according to claim 6, wherein the ratio of the weight of betaine hydrochloride to fluoride is from 1:15 to 1:40.

8. A lozenge according to claim 7, wherein the ratio of the weight of betaine hydrochloride to fluoride is between 0.55 and 17:1.

9. A lozenge according to claim 1, wherein said base includes a pharmaceutically acceptable gum.

10. A lozenge according to claim 1, wherein said base includes powdered gum and said sweetener includes sorbitol and mannitol.

11. A lozenge according to claim 1, wherein said base includes powdered gum and said sweetener includes sorbitol and mannitol, said betaine hydrochloride having a weight ratio to fluoride of between 17.1 and 0.55, said lozenge being effective for distributing its contents in the mouth for a period of at least two hours.

* * * * *